(12) United States Patent
Schaefer et al.

(10) Patent No.: US 10,723,989 B2
(45) Date of Patent: Jul. 28, 2020

(54) CONTAINER APPARATUS

(71) Applicant: Sartorius Stedim Biotech GmbH, Goettingen (DE)

(72) Inventors: Jan Schaefer, Edermuende (DE); Christian Manzke, Bovenden (DE); Etienne Evrard, Lathuy (BE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 15/576,081

(22) PCT Filed: May 12, 2016

(86) PCT No.: PCT/EP2016/000777
§ 371 (c)(1),
(2) Date: Nov. 21, 2017

(87) PCT Pub. No.: WO2017/005335
PCT Pub. Date: Jan. 12, 2017

(65) Prior Publication Data
US 2018/0148676 A1   May 31, 2018

(30) Foreign Application Priority Data
Jul. 6, 2015   (DE) ........................ 10 2015 008 766

(51) Int. Cl.
| | |
|---|---|
| *C12M 3/00* | (2006.01) |
| *B01J 19/00* | (2006.01) |
| *C12M 1/00* | (2006.01) |
| *C12M 1/06* | (2006.01) |
| *C12M 1/34* | (2006.01) |
| *C12M 1/36* | (2006.01) |

(52) U.S. Cl.
CPC ............ *C12M 23/48* (2013.01); *B01J 19/004* (2013.01); *C12M 23/52* (2013.01); *C12M 27/02* (2013.01); *C12M 29/14* (2013.01); *C12M 41/00* (2013.01); *C12M 41/48* (2013.01)

(58) Field of Classification Search
CPC ...... C12M 23/48; C12M 23/52; C12M 27/02; C12M 29/14; C12M 41/00; C12M 41/48; B01J 19/004
See application file for complete search history.

(56) References Cited

U.S. PATENT DOCUMENTS

| | | |
|---|---|---|
| 5,536,471 A | 7/1996 | Clark et al. |
| 6,281,005 B1 | 8/2001 | Casal et al. |

(Continued)

OTHER PUBLICATIONS

German Examination Report dated Apr. 12, 2016.
International Search Report dated Jul. 22, 2016.

*Primary Examiner* — William H. Beisner
*Assistant Examiner* — Danielle B Henkel
(74) *Attorney, Agent, or Firm* — Gerald E. Hespos; Michael J. Porco; Matthew T. Hespos

(57) ABSTRACT

The invention relates to a container device (1), comprising: a container receiving portion (4) for receiving a container; at least one valve (6) for controlling a flow of fluid in a fluid line connected to said container; a pump device (8) for generating a conveyor pressure of the fluid in the fluid line; a control device (10) which can be connected to the valve (6) and/or the pump device (8) in order to control the valve (6) and/or pump device (8); and a frame (2) which supports said container receiving portion (4), valve (6), pump device (8) and control device (10).

12 Claims, 4 Drawing Sheets

(56) References Cited

U.S. PATENT DOCUMENTS

| | | | |
|---|---|---|---|
| 6,425,414 B2 * | 7/2002 | Jorgensen | A61M 1/3693 137/597 |
| 6,506,890 B1 | 1/2003 | Cooper et al. | |
| 2005/0278066 A1 | 12/2005 | Graves et al. | |
| 2008/0139865 A1 * | 6/2008 | Galliher | B08B 15/02 588/249 |
| 2008/0160599 A1 * | 7/2008 | Weber-Matthiesen | C12M 23/50 435/286.2 |
| 2009/0035856 A1 * | 2/2009 | Galliher | C12M 23/14 435/383 |
| 2011/0008215 A1 | 1/2011 | Elizarov et al. | |
| 2012/0024490 A1 | 2/2012 | Tamai et al. | |

\* cited by examiner

CONTAINER APPARATUS

BACKGROUND

Field of the Invention

The present invention relates to a container apparatus.

Description of the Related Art

In the industry, container holders, called "palletanks," are used to hold disposable containers. The content of the disposable containers can be mixed, homogenized, transported (for example for filtering), tempered and/or simply stored in the container holders. Also, contents can be supplied to or conducted away from the disposable containers while the disposable container is situated in the container holder, with it being possible to weigh the content of the disposable container in the container holder. Furthermore, it is possible to carry out chemical and/or biological processes in the container holders.

Depending on the process to be carried out, the container holder must be moved to corresponding processing stations, in order to connect the container holder or the disposable container to corresponding apparatuses. The processing stations usually have a control apparatus for controlling the apparatuses, in each instance. If necessary, a sensor system present in the container holder and/or in the disposable container must be connected with the control apparatus of the corresponding processing station.

Handling of conventional container holders is very complicated, since the container holder with the disposable container must be moved to the corresponding processing station for every process to be carried out, and connected with the corresponding apparatuses there. Furthermore, the corresponding control apparatus must be configured for the process to be carried out, at every processing station.

It is therefore the task of the present invention to provide a container apparatus that is simpler to handle.

SUMMARY

According to the present invention, a container apparatus is provided, having: a container holder for holding a container; at least one valve for control of a fluid stream into a fluid line connected with the container; a pump apparatus for producing a conveying pressure of the fluid in the fluid line; a control apparatus that can be brought into connection with the valve and/or the pump apparatus, in order to control the valve and/or the pump apparatus; and a frame that carries the container holder, the valve, the pump apparatus, and the control apparatus.

It is advantageous that the container apparatus according to the invention makes it possible to integrate the apparatuses required for the processes that must typically be carried out, to produce a compact process unit. In this way, handling of the container apparatus is greatly simplified, since the need to connect the container apparatus with different apparatuses at different processing stations can be reduced or can actually be completely eliminated. Even if the container apparatus needs to be moved to a processing station, this happens in simple manner as a process unit, so that only the missing apparatuses or connections must be connected with the container apparatus. In this regard, it is furthermore advantageous that the processes to be carried out for a container can be carried out by means of a single control apparatus, which is a constant part of the process unit. This not only reduces the configuration effort of the control apparatus, but also improves the possibility of monitoring the processes.

The container holder can be configured essentially in block shape or cube shape. For example, the container holder can have an essentially tub-shaped main body and an essentially plate-shaped lid. The container holder can be configured to have a double wall, wherein the interstice between the inner wall and the outer wall can have a tempering medium flowing through it and/or can have lines for tempering media, in order to temper a holding space of the container holder. A container can be held, at least in part, in the container holder, particularly in its holding space, or a plurality of containers can be held, at least in part. The container holder can have one or more openings in one or more of the side walls and/or in the bottom and/or in the lid, in order to pass one or more hoses connected with the container, particularly fluid lines, to the outside. The container holder can have a holding volume or holding capacity of about 10 to 3000 liters, for example, preferably of about 50 to 500 liters. The container holder can be a "palletank," for example.

The container can be a disposable container, particularly a disposable plastic bag. The container can be a bioreactor bag, for example. However, the invention is not restricted to disposable plastic bags. The container can have one or more connectors, which can be connectors for filling, emptying, gasification and/or degasification. Hoses or fluid lines can be connected with the container by way of the connectors. The fluid lines can be, in particular, plastic hoses, preferably disposable plastic hoses. The container can have one or more integrated sensors, such as, for example, temperature, pressure, pH, conductivity and/or oxygen sensors, which can be connected with the control apparatus, for example by way of signal lines, a bus system and/or by way of a wireless connection (Bluetooth, WLAN, etc.). The container can furthermore have an integrated stirring system, addition ports and/or sample-taking systems. The content of the container can be mixed, homogenized, filtered, tempered and/or simply stored/transported in the container holder.

The valve serves for control of an inflow and/or outflow of the fluid in the fluid line to and/or from the container. The fluid that is supposed to flow in or out can also contain solids. The valve can be a contact-free valve, particularly a pinch valve. In the case of a pinch valve, the fluid line is pinched when the valve is activated, in order to reduce or interrupt the fluid stream through the fluid line. The pinch valve can be designed for hoses from ¼" to 1", preferably for ⅜" or ½" hoses. However, pinch valves can also be provided for both ⅜" hoses and ½" hoses. Activation can take place magnetically, pneumatically and/or hydraulically. However, the valve can also be a contact valve, for example a disposable membrane valve. The container apparatus can have a plurality of valves, for example 2 to 20 valves.

The pump apparatus serves for producing the conveying pressure of the fluid in the fluid line, wherein the conveying direction or pumping direction can be directed toward the container or away from the container. Recirculation of the fluid for thorough mixing in the container can be made possible by means of the pump apparatus. The pump apparatus does not necessarily have to be coupled with the same fluid line that is coupled with the valve. A fluid line can also be coupled only with the pump apparatus or only with the valve. Two fluid lines can also be provided, which are connected with the pump apparatus or with the valve, in each instance. The pump apparatus can have a contact-free pump, such as, for example, a peristaltic pump, into which a fluid line is inserted. However, the pump can also have a contact pump, for example a disposable membrane pump. The pump apparatus can have a plurality of pumps, by means of which conveying pressures can be produced in a plurality of fluid lines. Preferably, the pump apparatus has two pumps, particularly two peristaltic pumps, wherein one of the pumps serves for fluid feed, fluid discharge and/or fluid circulation, and the other pump can be used for titration processes. In this regard, the two pumps can be designed for throughputs of different sizes.

The control apparatus can be connected with the valve and/or the pump apparatus by way of signal lines, a bus system and/or by way of a wireless connection (Bluetooth, WLAN, etc.). The control device can be capable of being brought into connection with all the apparatuses and sensors required for the process to be carried out, preferably by way of signal lines, a bus system and/or by way of a wireless connection (Bluetooth, WLAN, etc.). The control apparatus can be designed for communicating with an external regulation apparatus, for example a computer, as an I/O box (input/output box), wherein the communication can take place by way of signal lines, a bus system and/or also by way of a wireless connection. The control apparatus can have I/O modules, bus interfaces, an energy supply and/or an emergency shut-off apparatus. The control apparatus can turn on the apparatuses connected with it, such as the valve and/or the pump apparatus. The control apparatus can also be designed to control, regulate and/or document the processes to be carried out. The processes to be carried out can comprise mixing processes, filtration processes, tempering processes, storage processes, titration processes, chemical reaction processes, biological reaction processes, filling processes, emptying processes, gasification processes and/or degasification processes.

The frame can be a welded construction composed of steel and/or aluminum profiles, for example square pipes. The frame can be configured essentially in block shape, and can have four outer, essentially vertical columns, which are connected by means of longitudinal profiles and/or plates and transverse profiles and/or plates. The container holder is preferably disposed essentially centered in the frame, and connected with it. The container holder can be disposed in or on the frame in such a manner that the contact surface of the container in the container holder lies at a height of about 50 cm to about 100 cm, which further simplifies handling of the container apparatus. The container holder, the valve, the pump apparatus, and the control apparatus are preferably separately connected with the frame and/or attached to it, in each instance. The attachment can take place, for example, by way of a screw connection and/or welded connection. The container holder can be mounted on the frame on rails, by means of which the container holder can be displaced relative to the frame, in order to simplify loading and unloading of the container into or out of the container holder.

Preferably, the container apparatus can furthermore have a weighing apparatus, wherein the frame carries the weighing apparatus.

The weighing apparatus serves for weighing the content of the container. The weighing apparatus is preferably also connected with the control apparatus, preferably by way of a signal line, a bus system and/or by way of a wireless connection (Bluetooth, WLAN, etc.). The information regarding the mass of the content of the container can be used for regulation of processes. Preferably, the weight of the container and of the fluid lines is tared before the start of the process. Alternatively or in addition, the container apparatus can have a fill level sensor that detects the volume of the content of the container, and is connected with the control apparatus.

Preferably, the weighing apparatus has at least one load cell, which is disposed between the container holder and the frame as a support of the container holder.

The container holder is particularly connected with the frame exclusively by way of the load cell. Preferably, the container holder has three load cells, which are preferably disposed at uniform intervals on the underside of the container holder, between the container holder and the frame. The load cells can be connected with the control apparatus, in each instance, for example by way of signal lines, a bus system and/or by way of a wireless connection (Bluetooth, WLAN, etc.). The weight of the container holder and, if applicable, of the tempering medium can be tared out.

Preferably, the frame has wheels and/or rollers on its underside, by means of which the container apparatus can be moved as a unit.

The wheels or rollers carry the total weight of the container apparatus. Back and forth movement of the container apparatus and thereby its handling are further simplified by means of the wheels or rollers. The frame can particularly have four wheels. The wheels are preferably disposed on the frame so as to pivot relative to a vertical axis.

Preferably, the container holder has a tempering medium inflow and a tempering medium outflow, which can be connected with a tempering regulation apparatus, in order to temper the container held in the container holder.

The container holder can be configured to have a double wall, wherein the interstice between the inner wall and the outer wall can be configured so that a tempering medium can flow through it, and/or can have tempering medium lines, in order to temper a holding space of the container holder. The tempering medium is supplied by way of the tempering medium inflow, and conducted away by way of the tempering medium outflow. Tempering medium inflow and outflow can have couplings for a simplified connection with the pipes or hoses of the tempering medium regulation apparatus. The tempering medium regulation apparatus can have a circulation pump for the tempering medium circuit, as well as a tempering actuator for cooling and/or heating, as well as corresponding sensors. The tempering medium regulation apparatus can be capable of being connected with the control apparatus, for example by way of a signal line, a bus system and/or by way of a wireless connection (Bluetooth, WLAN, etc.), and can be turned on or regulated by this apparatus. The tempering medium regulation apparatus can also be disposed on the frame and represent part of the container apparatus. The tempering medium inflow and/or the tempering medium outflow can also be connected with the control apparatus.

Preferably, the container apparatus has a stirring apparatus, which is disposed on the frame and below the container holder.

The stirring apparatus can also be capable of being connected with the control apparatus, for example by way of a signal line, a bus system and/or by way of a wireless connection (Bluetooth, WLAN, etc.), and can be turned on or regulated by this apparatus. The stirring apparatus is also carried by the frame. The stirring apparatus is preferably a magnetic stirrer, in which a stirring element disposed in the container is magnetically put into rotation.

Preferably, the valve is a pinch valve, and/or the pump apparatus has a peristaltic pump.

Preferably, the container holder has a passage opening for passing the fluid line through, wherein the valve is disposed on the frame in the region of the passage opening.

The passage opening can be configured for passing a plurality of fluid lines through the wall of the container holder. Preferably, the container holder has a passage opening on a side wall, wherein at least one valve is disposed on the frame, particularly on a vertical column thereof, in the region of the passage opening.

Preferably, the control apparatus has a bus system for communicating with an external apparatus.

The external apparatus can be an external computer, wherein communication can take place by way of a signal line, a bus system and/or by way of a wireless connection. The process to be carried out can be configured, controlled or regulated, documented and/or evaluated in simple manner, by means of the computer.

Preferably, the control apparatus has an input apparatus.

The input apparatus can be an input panel, for example. The control apparatus can furthermore have a display device, for example a monitor or a display. The control apparatus can also have a touchpad, which combines an input apparatus and a display device. Processes can be carried out without using an external apparatus, by means of the input apparatus.

DETAILED DESCRIPTION

Figure 1:
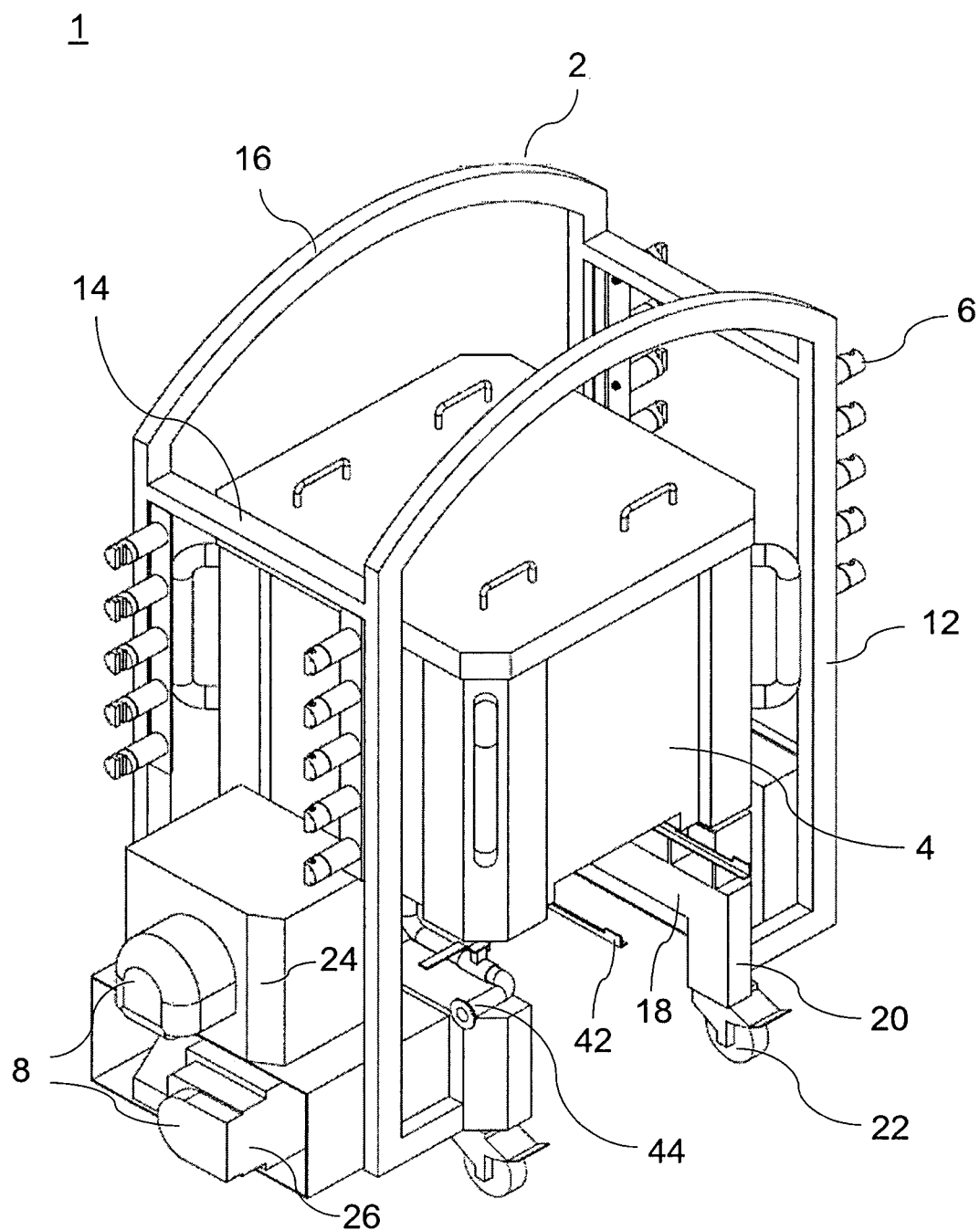
FIG. 1 a perspective view of a container apparatus according to one embodiment.
Figure 2:
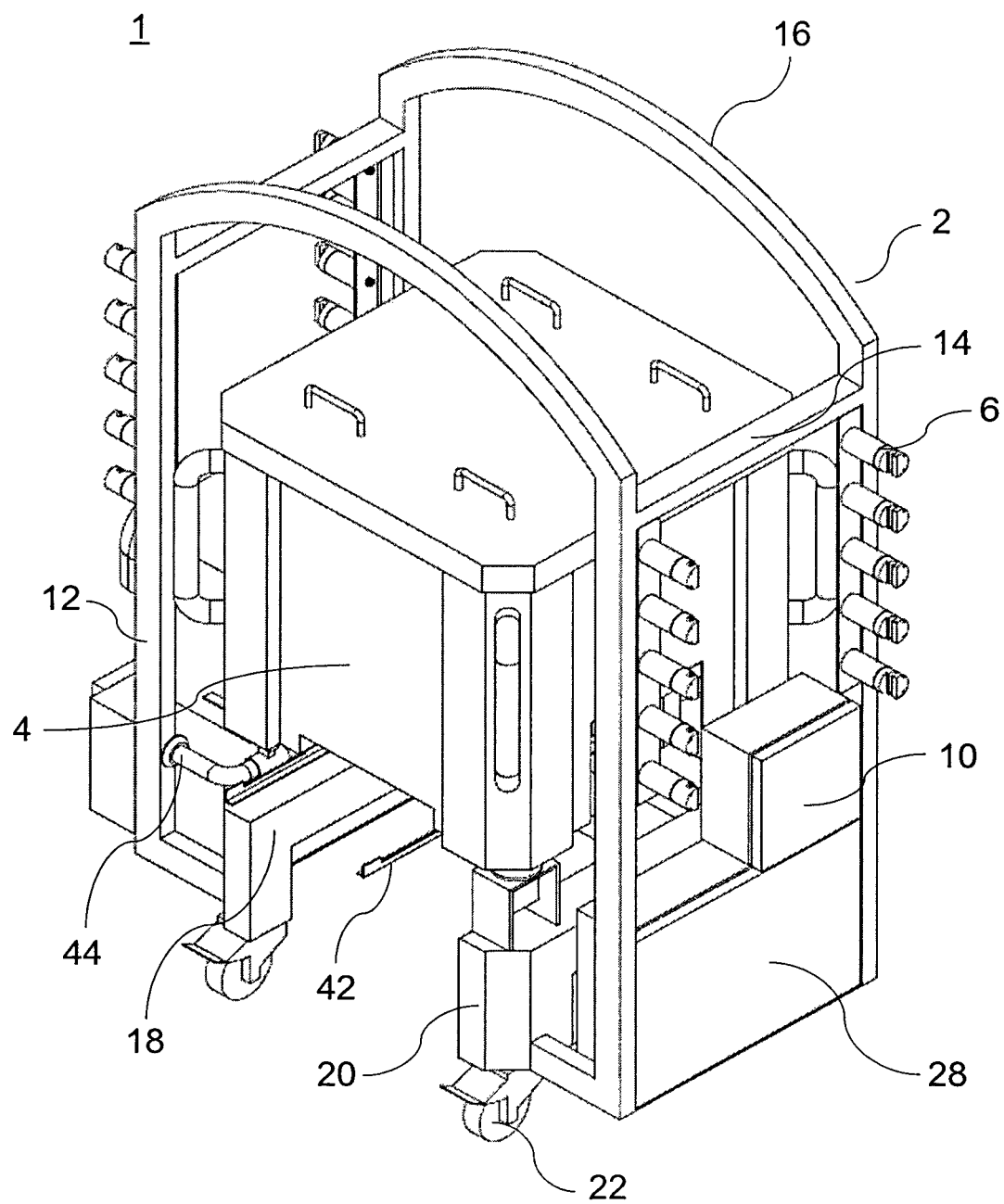
FIG. 2 a further perspective view of the container apparatus according to the embodiment.

FIG. 1 and FIG. 2 each show perspective views of a container apparatus 1 according to one embodiment, from different viewing angles. The container apparatus 1 has a frame 1, on which a container holder 4, a plurality of valves 6, a pump apparatus 8, and a control apparatus 10 are disposed. The frame 2 carries the container holder 4, the valves 6, the pump apparatus 8, and the control apparatus 10.

The frame 2 according to the embodiment is essentially a welded construction composed of square pipes, and has four outer, essentially vertical columns 12, which are connected by means of essentially horizontal transverse profiles 14 and longitudinal profiles 16. The frame 2 furthermore has a framework section 18 in the center, which particularly serves as a support for the container holder 4. The four essentially vertical framework legs 20 have wheels 22, which are mounted so as to pivot, in each instance, on their lower ends. A parking brake can be disposed on the wheels 22, in each instance, preferably at least on two of the wheels 22, in each instance. The wheels 22 carry the weight of the container apparatus 1 and allow easy moving of the container apparatus 1. The frame 2 and the container apparatus 1 have a narrow side and a broad side.

The pump apparatus 8 has a first peristaltic pump 24 and a second peristaltic pump 26. The first peristaltic pump 24 can be used, for example, for filling or emptying the container (not shown) or for recirculation of the fluid in the container. The second peristaltic pump 26 can be used for titration, for example, preferably in combination with the valves 6. Both the first peristaltic pump 24 and the second peristaltic pump 26 are connected with the control apparatus 10 by means of signal lines (not shown), and are turned on by this apparatus. The pump apparatus 8 is disposed between two columns of the narrow side of the frame 2, on a lower, side section of the frame 2.

The valves 6 are turned on by the control apparatus 10. For this purpose, the control apparatus 10 is connected with the valve control box 28 of the valves 6 by way of a signal line (not shown). The container apparatus 1 has twenty valves 6, which are disposed on the columns 12 of the frame 2 in groups of five, in each instance, essentially at the height of the container holder 4. The valves 6 are configured as pinch valves and each have a holding groove for the fluid lines (not shown) of the container (not shown). The control apparatus 10 and the valve control box 28 are disposed opposite to the pump apparatus 8, between two columns of the narrow side of the frame 2, on a lower, side section of the frame 2. The control apparatus 10 and the pump apparatus 8 are therefore disposed on two opposite sides of the frame 2, wherein the container holder 4 is disposed essentially centered between the control apparatus 10 and the pump apparatus 8.

Figure 3:
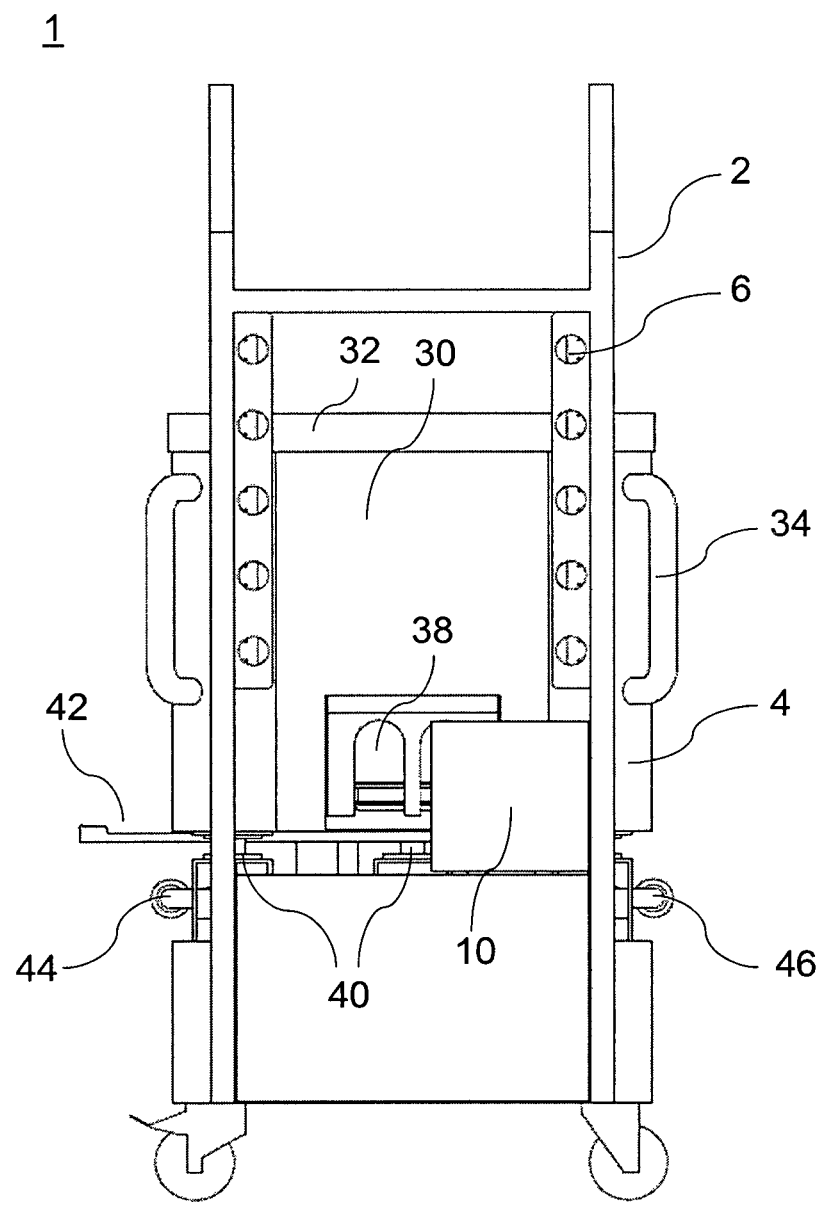
FIG. 3 a side view of the container apparatus according to the embodiment.
Figure 4:
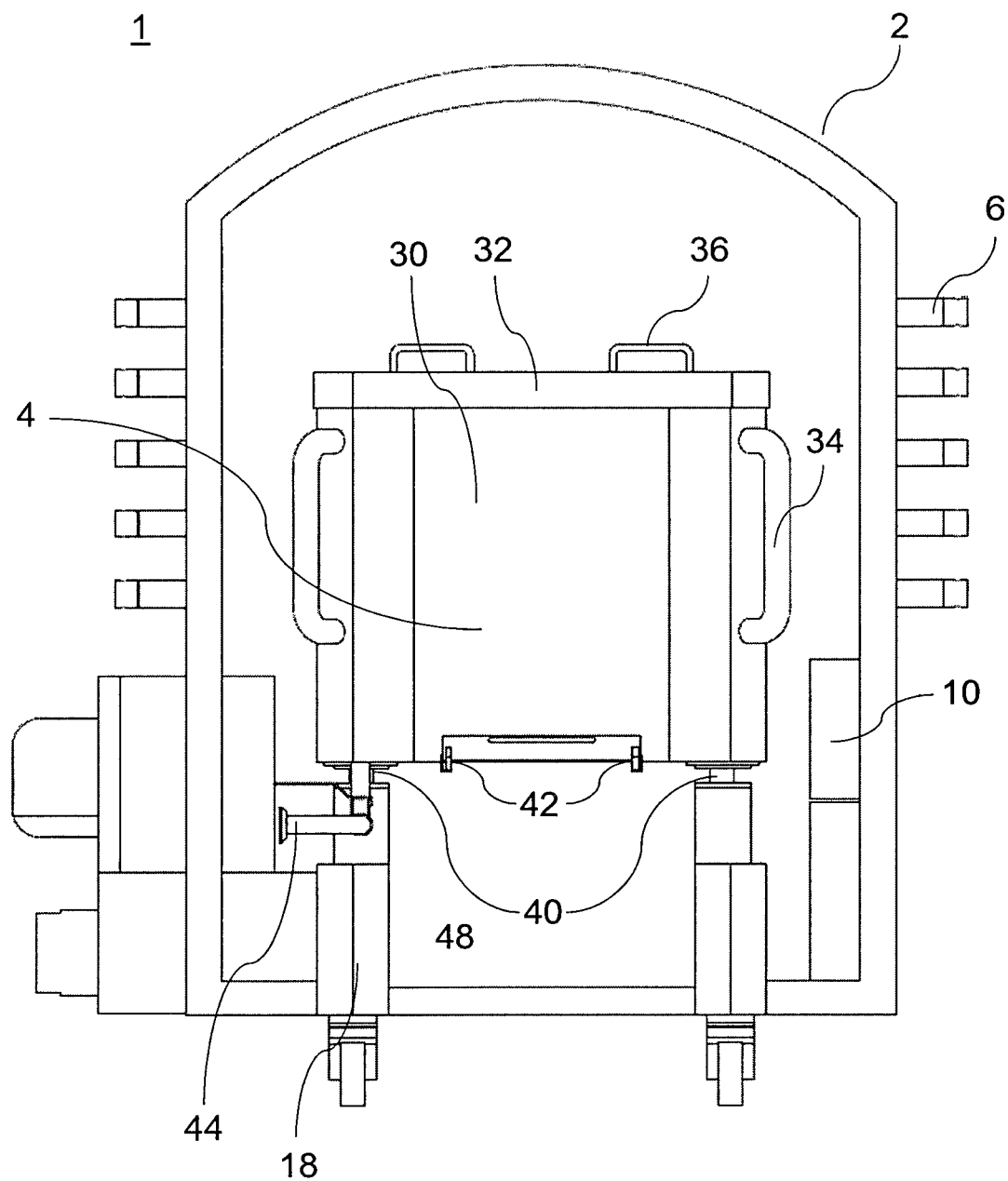
FIG. 4 a further side view of the container apparatus according to the embodiment.

FIG. 3 shows a side view of the narrow side of the container apparatus 1, and FIG. 4 shows a side view of the broad side of the container apparatus 1. The container holder 4 is configured essentially in block shape or cube shape, and has an essentially tub-shaped main body 30 and an essentially plate-shaped lid 32. However, the form of the container holder 4 is not restricted to this, and can also be configured to be cylindrical, for example. For simplified moving of the container holder 4, the main body 30 has manipulation handles 34 at the four outer corners of the body. For simplified lifting of the lid 32, the lid 32 has four lid handles 36.

The container holder 4 has a passage opening 38, which is open toward the narrow side of the container apparatus 1, on a side wall of the main body 30. Fluid lines that are connected with the container can be passed through the passage opening 38, from the outside into the interior of the container holder 4. The passage opening 38 is dimensioned in such a manner that a possible tempering function of the container holder 4 is not impaired. The passage opening 38 is preferably large enough so that at least twenty fluid lines, corresponding to the number of valves 6, can be passed through.

The container holder 4 is connected with the frame 2, particularly the framework section 18 of it, by way of three load cells 40. The load cells 40 represent the supports for the container holder 4. The load cells 40 are connected with the control apparatus 10 by way of signal lines. The container holder 4 furthermore has a rail system 42, by means of which the container holder 4 can be displaced relative to the frame 2, particularly can be pushed sideways out of a central region of the frame 2. In this way, loading and unloading of the container holder 4 is simplified.

The container holder 4 or the main body 30 of it is configured to have a double wall. Tempering medium or tempering medium lines can be accommodated in the interstice between the inner wall and the outer wall of the container holder 4. In the present embodiment, a tempering medium regulation apparatus (not shown) is not part of the container apparatus 1. Therefore the container holder 4 has only a tempering medium inflow 44 and a tempering medium outflow 46, which are disposed on the underside of the container holder 4. An external tempering medium regulation apparatus, by means of which the interior of the container holder 4 can be tempered, can be connected by way of the tempering medium inflow 44 and the tempering medium outflow 46. The external tempering medium regulation apparatus can be connected with the control apparatus 10 by way of a signal line, and turned on by this apparatus.

In the present embodiment, a stirring apparatus (not shown) is furthermore not part of the container apparatus 1. For this reason, the frame 2 or the framework section 18 of it has a free space 48 below the container holder 4, so that an external stirring apparatus, particularly a magnetic stirrer, can be pushed below the container holder 4 from the side, in order to stir the content of the container. The external stirring apparatus can be connected with the control apparatus 10 by way of a signal line, and turned on by this apparatus.

The control apparatus 20 is connected with the valves 6 and the pump apparatus 8 by way of signal lines, a bus system and/or by way of a wireless connection (Bluetooth, WLAN, etc.). The control apparatus 20 is brought into connection with all of the apparatuses and sensors required for the process to be carried out, with the connections being achieved by way of signal lines, a bus system and/or by way of a wireless connection (Bluetooth, WLAN, etc.). The control apparatus 20 can be designed for communicating with an external regulation apparatus, for example a computer, as an I/O box (input/output box), so that the communication can take place by way of signal lines, a bus system and/or also by way of a wireless connection. The control apparatus 20 has I/O modules, bus interfaces, an energy supply and/or an emergency shut-off apparatus. The control apparatus 20 can turn on the apparatuses connected with it, such as the valves 6 and/or the pump apparatus 8. The control apparatus 20 also preferably is designed to control, regulate and/or document the processes to be carried out. The processes to be carried out can comprise mixing processes, filtration processes, tempering processes, storage processes, titration processes, chemical reaction processes, biological reaction processes, filling processes, emptying processes, gasification processes and/or degasification processes. The control apparatus 20 preferably has an input device. The input device of the control apparatus 20 can be an input panel. The control apparatus 20 further can have a display device, such as a monitor or a display. Additionally, the control apparatus 20 can have a touchpad that combines an input device and a display device. Processes can be carried out without using an external apparatus by means of the input device of the control apparatus 20.

REFERENCE SYMBOL LIST 1 container apparatus
2 frame
4 container holder
6 valve
8 pump apparatus
10 pump apparatus
12 column
14 transverse profile
16 longitudinal profile
18 framework section
20 framework leg
22 wheel
24 first peristaltic pump
26 second peristaltic pump
28 valve control box
30 main body
32 lid
34 manipulation handle
36 lid handle
38 passage opening
40 load cells
42 rail system
44 tempering medium feed
46 tempering medium discharge
48 free space

The invention claimed is:

1. A container apparatus (1), having:
   a frame (2) having a framework section (18) and supports (12, 14, 16) supported by the framework section (18) and disposed at least partly above the framework section (18), the supports (12, 14, 16) including vertical supports (12) defining a container receiving space inward of the vertical supports (12) and above the framework section (18);
   a weighing apparatus (40) supported on the framework section (18);
   a container holder (4) displaceable sideways relative to the vertical supports and to a position in the container receiving space where the container holder (4) is supported on the weighing apparatus, the container holder (4) being configured for holding a container;
   plural valves (6) mounted on the frame (2), at least a first of the plural valves (6) being operative for control of a fluid stream into a fluid line connected with the container;
   a pump apparatus (8) mounted on the frame (4), the pump apparatus (8) comprising plural peristaltic pumps (24, 26), at least a first of the plural peristaltic pumps (24) that is mounted on the frame (4) being for producing a conveying pressure of the fluid in the fluid line and at least a second of the plural peristaltic pumps (26) being configured for titration; and
   a control apparatus (10) mounted on the frame (4) and connected with the weighing apparatus (40), the plural valves (6) and the pump apparatus (8), in order to control the plural valves (6) and/or the pump apparatus (8) based at least partly on output of the weighing apparatus (40).

2. The container apparatus (1) according to claim 1, wherein the weighing apparatus (40) has at least one load cell (40).

3. The container apparatus (1) according to claim 1, wherein the frame (2) has wheels (22) and/or rollers on its underside, by means of which the container apparatus (1) can be moved as a unit.

4. The container apparatus (1) according to claim 1, wherein the container holder (4) has a tempering medium inflow (44) and a tempering medium outflow (46) that can be connected with a tempering regulation apparatus to temper the container held in the container holder (4).

5. The container apparatus (1) according to claim 1, wherein the container apparatus (1) has a stirring apparatus disposed on the frame (2) and below the container holder (4).

6. The container apparatus (1) according to claim 1, wherein the at least one valve (6) is a pinch valve, and/or wherein the pump apparatus (8) has a peristaltic pump (24, 26).

7. The container apparatus (1) according to claim 1, wherein the container holder (4) has a passage opening (38) for passing the fluid line through, and wherein the at least one valve (6) is disposed on the frame (2) in the region of the passage opening (38).

8. The container apparatus (1) according to claim 1, wherein the control apparatus (10) has a bus system for communicating with an external apparatus.

9. The container apparatus (1) according to claim 1, wherein the control apparatus (10) has an input apparatus.

10. The container apparatus (1) according to claim 1, further comprising a lid (32) mounted on the container holder (4) and configured for defining a space for receiving the container.

11. The container apparatus (1) according to claim 1 wherein the frame (2) includes vertical columns extending up from the framework section (18), the at least one valve (6) being mounted to at least one of the vertical columns (12).

12. The container apparatus (1) according to claim 1, further comprising rails on the framework section (18) and movably accommodating the container holder (4) and enabling movement of the container holder (4) away from the frame (2).

\* \* \* \* \*